(12) United States Patent
Saugstad et al.

(10) Patent No.: US 6,838,441 B1
(45) Date of Patent: Jan. 4, 2005

(54) ALBUMIN FOR TREATING MECONIUM ASPIRATION SYNDROME

(76) Inventors: Ola Didrik Saugstad, Department of Pediatric Research, The National Hospital, N-0027 Oslo (NO); Christian André Drevon, Institute for Nutrition Research, University of Oslo P.O. Box 1046 Blindern, N-0316 Oslo (NO)

( * ) Notice: Subject to any disclaimer, the term of this patent is extended or adjusted under 35 U.S.C. 154(b) by 35 days.

(21) Appl. No.: 10/110,182

(22) PCT Filed: Sep. 15, 2000

(86) PCT No.: PCT/NO00/00301

§ 371 (c)(1),
(2), (4) Date: Apr. 8, 2002

(87) PCT Pub. No.: WO02/11755

PCT Pub. Date: Feb. 14, 2002

(30) Foreign Application Priority Data

Aug. 7, 2000 (GB) .............................................. 0019378

(51) Int. Cl.⁷ ............................................... A61K 38/38
(52) U.S. Cl. ............................... 514/21; 514/2; 514/10; 514/11; 514/12; 514/13; 514/14
(58) Field of Search ................................. 514/2, 10, 11, 514/12, 13, 14, 912

(56) References Cited

U.S. PATENT DOCUMENTS 6,043,213 A    3/2000   Tsubota

OTHER PUBLICATIONS

Tollofsrud, " Inhibition of meconium free fatty acids (FFA) by bovine serum albumin (BSA) in newborn piglets with meconium aspiration (MA)", 2000, Pediatric Research, vol. 47, #4, part 2, pp 378A.*

Lam, " Surfactant lavage for meconium aspiration syndrome: a pilot study", 1999, Pediatrics, vol. 103, pp. 1014–1018.*

Srinivasan, "Meconium aspiration syndrome: current concepts and management", 1999, Comp. Ther., vol. 25, #2, pp. 82–89.*

Srinivasan, H.B., and Vidyasagar, D., Comp. Ther. 25(2): 82–89 (1999).

Terasaka, D., et al., Biol. Neonate 50: 16–20 (1986).

Tollofsrud, P.A., Ped. Res. 47(4), Part 2: 378A (2000) Abstract 2233.

* cited by examiner

Primary Examiner—Christopher Tate
Assistant Examiner—Roy Teller
(74) Attorney, Agent, or Firm—St. Onge Steward Johnston & Reens LLC

(57) ABSTRACT

The present invention provides a method of treating meconium aspiration syndrome, said method comprising administering to a subject in need of treatment a therapeutically effective amount of albumin. A further aspect of the invention relates to the use of albumin in the preparation of a medicament for treatment of meconium aspiration syndrome, and a pharmaceutical composition comprising albumin admixed with a pharmaceutically acceptable carrier, diluent or excipient.

14 Claims, No Drawings

ALBUMIN FOR TREATING MECONIUM ASPIRATION SYNDROME

The present invention relates to a method of medical treatment. More specifically, the invention relates to a method of treating meconium aspiration syndrome in newborn infants.

The first stool of a newborn baby, known as meconium, is typically thick, viscous, sticky and green. Occasionally during the child birth process, meconium can be aspirated into the lungs of the newborn infant inducing severe lung injury and lung failure. This condition is known as Meconium Aspiration Syndrome (MAS) and usually occurs in full term or post term infants, often small for their gestational age, either in the uterus or with their first breath.

Meconium stained amniotic fluid (MSAF) is present in approximately 13% of all births in the USA. Of these, some 5 to 12% develop MAS, a figure which represents about 26,000 newborn infants in the USA alone (Wiswell TE, Bent RC, Pediatr Clin North Am 1993;40:955–981, Cleary GM, Wiswell TE, Pediatr Clin North Am 1998;45:511–529, Wiswell TE et al, Pediatrics 2000;105:1–7). In developing countries in particular, it is fared that MAS represents an even more serious threat than in the Western world (Adhikar M, Gouws ES, Afr Med J 1995;85:891–893, Gupta V et al, Indian J Pediatr 1996;33:293–297). Recent statistics indicate that 400/o of infants in need of resuscitation have meconium stained amniotic fluid (Saugstad et al, Pediatrics 1998). Thus, out of the 130 million annual births worldwide it is estimated that aproximately 15 million newborn infants aspirate meconium and 750 000 to 1.8 million of these develop MAS.

MAS involves progressive respiratory distress, hypoxia, hypercapnia, and acidosis, thereby necessitating long-term ventilatory treatment. Hypoxia is caused by a reduction in the oxygen supply to tissues to below physiological levels, despite adequate person of the tissue by the blood, whereas hypercapnia refers to a condition in which there is an excess of carbon dioxide in the blood. Severe cases of MAS require extracorporeal membrane oxygenation (ECMO) for survival (Toomasian et al, ASAID Trans 1988 34:140147). Mortality rates vary between 4–12% (Wiswell TE, Bent RC, ibid 1993, Coltar et at, Br J Obstet Gynecol 1999;96:411–414, Davis et at, Am J. Obstet Gynecol 1985;151:731–736, Faleiglia Obstet Gynecol 1988;71:349–353), representing approximately 30,000 to 200,000 deaths annually. Any reduction in the mortality rate could therefore save a vast number of lives.

In addition to hypoxia, hypercapnea and acidosis, meconium aspiration can also result in hypoxemia (deficient oxygenation of arterial blood), vascular shunting and decreased lung compliance, as well as the collapse of subpleural alveoli with the development of gross and microscopic atelectasis (Clark et al, J Pediatr 1987;110:765–770, Sun B et al, Biol Neonat 1993;63:96–104, Sun B et at, J Appl Physiol 1994;77:1961–1971. Atelectasis (partial or complete collapse of the lung) may result from mechanical obstruction caused by the particulate meconium and from chemical pneumonitis and meconium inhibition of surfactant. While mechanical obstruction may play a role in meconium-induced pulmonary injury, the use of filtered meconium (which eliminates mechanical obstruction), has been shown to lead to a loss of pulmonary function and alveolar collapse (Chen et at, Crit Care Med 1985;13:233–236). Such observations suggest that meconium has a direct in vivo effect on the lungs.

Further research has shown that meconium instilled in the lung induces an inflammatory response, including pulmonary hypertension, probably by invoking thromboxane A2 and prostacyclin. It has also been established that human meconium exhibits high phospholipase A2 activity (Soukka H et al, Pediatr Res 1997;23:205–211, Soukka H et al, Pediatr Res 1997;42:145–150, Holopainen R et al, Pediatr Pulmonol 1998;25:107–113, Soukka H et al, Pediatr Res 1998;44:838–842, Holopainen R et al, Pediatr Res 1999;46:626–632).

To date, MAS has been treated with only moderate success using surfactant instillation (Soll RF et al, Database Syst Rev 2000; (2):CD002054; Halliday HL et al, Eur J Pediatr 1996;155:1047–1051), amnioninfusion and lavage with surfactant (Lam BC et al, Pediatrics 1999;103:1014–1018). However, up to now, there have been no significant advances in the treatment of this condition.

The present invention thus seeks to provide an improved method of treating MAS which is more effective than the methods currently employed in clinical practice.

Aspects of the invention are presented in the accompanying claims and in the following description.

In a first aspect, the invention provides a method of treating meconium aspiration syndrome, said method comprising administering to a subject in need of treatment a therapeutically effective amount of albumin.

By way of definition, the term "albumin" refers to any one of a group of proteins that are soluble in water and moderately concentrated salt solution, and that are coagulable on heating. Suitable albumins will be familiar to those skilled in the relevant art. Typical examples of albumins useful in the present invention include plasma albumin, ovalbumin, lactalburnin and soybean albumin. In addition, these proteins may be modified by proteolysis, sequence modification using molecular biological methods, and by binding to lipids or carbohydrates.

In a first preferred aspect of the invention, the albumin is serum albumin, more preferably bovine serum albumin.

In a second preferred aspect of the invention, the albumin reduces the toxicity of meconium. In other words, by specifically inhibiting potentially toxic substances contained in meconium, the present invention provides a new therapeutic method for treating MAS.

In a third preferred aspect of the invention, the albumin binds to lipids in meconium, in particular, free fatty acids.

By way of definition, the term "lipid" encompasses a diverse range of orgainc compounds which are insoluble in water but soluble in organic solvents, and includes both complex and simple lipids. Complex lipids are esters of long-chain fatty acids which include, for example, glycerides, glycolipids and phospholipids. Simple lipids do not contain fatty acids and include, for example, steroids (such as adrenal hormones, sex hormones and bile acids) and terpenes (such as vitamins A, E and K).

The term "fatty acid" refers to an organic compound consisting of a hydrocarbon chain and a terminal carboxyl group. Typically, the chain may contain from 1 to about 30 carbon atoms and may be saturated, unsaturated or polyunsaturated, and may be branched or unbranched Recent research has established that meconium contains a high concentration of free fatty acids (Tollofsrud et al, unpublished) which may have toxic effects on the lung. Accordingly, the present invention seeks to alleviate the symptoms of MAS by binding free fatty acids present in meconium, thereby reducing the pulmonary toxicity.

Studies have also indicated that meconium typically contains high levels of bile acids. As with free fatty acids, bile acids can also lead to severe pulmonary toxicity problems.

Thus, in another preferred aspect, the method of the invention further comprises administering a therapeutically effective amount of one or more bile acid blockers.

For the purposes of this invention, the term "bile acid blocker" refers to any species which is capable of binding to one or more bile acids.

An example of such a bile acid blocker is cholestyramin, which is able to bind bile acids in exchange for chloride ions. Antibodies against bile acids may also be suitable bile acid blockers for the purposes of the present invention.

By way of definition, the term "antibody" includes but is not limited to, polyclonal, monoclonal, chimeric, single chain, Fab fragments, fragments produced by a Fab expression library, as well as mimetics thereof. Such fragments include fragments of whole antibodies which retain their binding activity for a target substance, Fv, F(ab') and F(ab')$_2$ fragments, as well as single chain antibodies (scFv), fusion proteins and other synthetic proteins which comprise the binding site of the antibody.

In a particularly preferred aspect of the invention, the bile acid blockers inhibit the effects of bile acids in meconium.

The principle described herein thus centres on the administration of albumin, or albumin derivatives, either alone or in combination with bile acid blockers into newborn infants with meconium aspiration.

Preferably, the albumin and/or bile acid blockers are administered into the trachea of the newborn infant Typically, a physician will determine the actual dosage of albumin, or albumin derivatives, and/or bile acid blockers that will be most suitable for an individual patient and this will vary with the age, weight and response of the particular patient.

Studies have been carried out on piglet lungs to compare the effect of (i) meconium, (ii) meconium from which the lipids (including fatty acids) have been extracted ("lipid-free meconium"), and (iii) meconium from which the bile acids have been extracted ("bile acid-free meconium"). After 4 and 6 hours, the group treated with lipid-free meconium, and bile acid-free meconium required significantly less oxygen than the group treated with meconium alone. In addition, lung compliance was significantly better for piglet lungs treated with lipid-free meconium and bile acid-free meconium than for treatment with meconium alone. Such results clearly suggest that the acute changes observed in newborn infants with MAS are to some extent attributable to the presence of lipids and water-soluble components (such as bile acids) in meconium.

In order to ensure effective delivery to the smallest airways of the lung, the administration of albumin, or derivatives thereof, and/or bile acid blockers may be coupled to surfactant instillation.

Thus, in yet another preferred aspect, the method of the invention further comprises administering a therapeutically effective amount of one or more surfactants.

Typically, the albumin, or derivative thereof, and/or bile acid blockers may be administered consecutively, simultaneously or sequentially with the surfactant, preferably either immediately before or immediately after surfactant instillation.

By way of definition, the term "surfactant" refers to any substance added to a liquid that is capable of increasing its spreading or wetting properties by reducing its surface tension. Typical surfactants suitable for use in the present invention include surfactant extracted from minced porcine lungs or extracted from bovine lungs. Artificial and recombinant surfactants are also suitable for use in the present invention.

Again, a physician will determine the actual dosage of surfactant that will be most suitable for an individual patient and this will vary with the age, weight and response of the particular patient.

A second aspect of the invention relates to the use of albumin in the preparation of a medicament for treating meconium aspiration syndrome.

In a preferred aspect, the albumin reduces the toxicity of meconium.

In a particularly preferred aspect, the albumin is serum albumin, more preferably bovine serum albumin.

A further preferred aspect of the invention relates to the use of albumin in the preparation of a medicament for eing meconium aspiration, wherein said albumin is administed in conjunction with one or more bile acid binding components.

In an alternative preferred aspect, the albumin is administered in conjunction with one or more surfactants.

As used herein the phrase "preparation of a medicament" includes the use of albumin, or a derivative thereof, directly as the medicament in addition to its use in a screening programme for the identification of further active agents or in any stage of the manufacture of such a medicament.

Such a screening programme may for example include an assay for determining whether a candidate substance is capable of mimicking the activity of albumin and/or bile acid blockers in the context of the present invention.

A third aspect of the invention relates to a pharmaceutical composition comprising albumin admixed with a pharmaceutically acceptable carrier, diluent, excipient, or combinations thereof.

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical a and are described, for example, in Remington's Pharmaceutical Sciences, Mack Publishing Co. (A. R. Gennaro edit 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

In a preferred aspect, the composition of the invention further comprises one or more bile acid blockers, as described hereinbefore.

In another preferred aspect, the composition of the invention further comprises one or more surfactants, as described hereinbefore.

It will be appreciated by those skilled in the art that the active agent(s) of the present invention may be delivered in the form of a prodrug. By way of example, a prodrug includes any entity having one or more protected group(s) and which may not possess pharmacological activity per se, but may, in certain instances, be administered and thereafter metabolised in the body to form the pharmaceutically active agent of the present invention.

The skilled person in the art will further appreciate that certain moieties known as "promoieties", for example as described in "Design of Prodrugs" by H. Bundgaard, Elsevier, 1985 (the disclosured of which is hereby incorporated by reference), may be placed on appropriate functionalities of the active agent. Such prodrugs are also intended to fall within the scope of the present invention.

The present invention will now be described only by way of example.

EXAMPLE 1

Animal Model

Meconium was obtained from the first stool of healthy newborn infants and free fatty acid content (FFA) was estimated to be, on average, 23.9 nanomol/mg meconium dry weight. In order to neutralize the FFA, bovine serum albumin was added in a 1:1 molar ratio (i.e 157 mg per ml meconium).

An animal model was developed using newborn piglets 0–2 days old. Meconium (3 ml/kg) with or without bovine serum albumin was instilled in the piglets lungs after a brief but serious episode of hypoxemia induced by 8% oxygen in the inspiration air. Systemic and pulmonary hemodynamics were monitored. Proinflammatory cytokines (TNF, IL-8) were measured in tracheal aspirate (Groneck P et al, Pediatrics 1994; 93:712–713), as well as surfactant function. An investigation into lung morphology was also carried out.

Experiments were carried out to compare the effects of administering bovine serum albumin and meconium to animals, with the adminstration of meconium alone. The results demonstrated that the meconium/albumin group exhibit a significantly higher lung compliance, a lower mean airway pressure, and a lower inspired fraction of oxygen. For example, the fraction of oxygen in inspired air was close to 0.21 in the meconium/albumin group compared with approximately 0.30 in the group given meconium alone. Furthermore, the levels of IL-8 increased significantly in the meconium group, whereas no increase was observed in the meconium/albumin group. This latter effect could not be attributed to specific inhibition of IL-8 by albumin since in vitro studies adding a similar amount of albumin to the IL-8 assay had no influence on the measurements. No differences were observed between the groups with regard to lung morphology, surfactant function, or pulmonary hemodynamics although there was a tendency towards lower pulmonary arterial pressure in the meconium/albumin group.

EXAMPLE 2

The same experimental model was used as described in Example 1. Newborn piglets bad instilled into their lungs either (i) meconium, (ii) meconium from which the lipids have been extracted ("lipid-free meconium"), and (iii) meconium from which the water-soluble components, such as bile acids, have been extracted ("bile acid-free meconium"). In the two latter groups the fraction of oxygen in inspired air was close to 0.21 at 4 hours of age, compared with approximately 0.35 im the first group. Lung compliance was significantly higher in the two latter groups compared with the first group.

Clinical Protocol in Infant Subjects

Bovine serum albumin, bovine serum albumin derivatives and/or bile acid inhibitors may be instilled into the lungs using the calculated optimal dose based on previous dose-response studies in animals. The infant is intubated tracheally and a feeding tube is inserted inside the tube down to the carina and withdrawn 2 mm. The meconium blocker is then rapidly instilled into the tube. The infant is ventilated by hand for a minute before recoupling to the ventilator. All vital sign variables are then monitored. The short term effects can be monitored by observing oxygenation and acid base status. Longer term effects may be assessed by monitoring the time spent on a ventilator, the time in greater than 40% oxygen, the rate of progression of chronic lung disease, and the overall survival rate.

Various modifications and variations of the described methods of the invention will be apparent to those skilled in the art without departing from the scope and spirit of the invention. Although the invention has been described in connection with specific preferred embodiments, various modifications of the described modes for carrying out the invention which are obvious to those skilled in the relevant art are intended to fall within the scope of the following claims.

What is claimed is:

1. A method of treating meconium aspiration syndrome, said method comprising administering to a subject in need thereof a therapeutically effective amount of albumin.

2. The method according to claim 1 wherein albumin is serum albumin.

3. The method according to claim 1 wherein said albumin reduces the toxicity of meconium.

4. The method according to claim 1 wherein said albumin binds lipids in meconium.

5. The method according to any of claims 1–4 which further comprises administering a therapeutically effective amount of one or more bile acid blockers.

6. The method according to claim 5 wherein said bile acid blockers bind bile acids in meconium.

7. The method according to claim 1 wherein said albumin is administered into the trachea of said subject.

8. The method according to claim 1 which further comprises administering a therapeutically effective amount of one or more surfactants.

9. The method according to claim 2 wherein said albumin is bovine serum albumin.

10. The method according to claim 4 wherein said lipids comprise fatty acids.

11. The method of treating an infant presenting with meconium aspiration syndrome comprising administering to the trachea of the infant an effective amount of serum albumin and a surfactant.

12. The method according to claim 11 wherein the albumin is administered consecutively, simultaneously, or sequentially with the surfactant.

13. The method according to claim 12 wherein the albumin and surfactant are administered simultaneously as a pharmaceutical composition containing both ingredients.

14. The method according to claim 11 wherein a bile acid blocker is also administered to the infant.

* * * * *